United States Patent [19]

van 't Klooster

[11] Patent Number: 6,126,970
[45] Date of Patent: Oct. 3, 2000

[54] CISAPRIDE SUSTAINED RELEASE

[75] Inventor: Gerben Albert Eleutherius van 't Klooster, Breda, Netherlands

[73] Assignee: Janssen Pharmaceutica N.V., Beerse, Belgium

[21] Appl. No.: 09/142,245

[22] PCT Filed: Nov. 26, 1996

[86] PCT No.: PCT/EP96/05346

§ 371 Date: May 21, 1998

§ 102(e) Date: May 21, 1998

[87] PCT Pub. No.: WO97/20562

PCT Pub. Date: Jun. 12, 1997

[30] Foreign Application Priority Data

Dec. 1, 1995 [EP] European Pat. Off. .............. 95203309

[51] Int. Cl.[7] ................ A61K 9/22; A61K 9/32
[52] U.S. Cl. .......... 424/482; 424/468; 424/474; 424/475; 514/772.2; 514/772.3
[58] Field of Search ...................... 424/464, 465, 424/468, 474, 475, 482, 472, 473, 480, 479

[56] References Cited

FOREIGN PATENT DOCUMENTS

| 0 076 530 | 4/1983 | European Pat. Off. . |
| 0 211 991 | 3/1987 | European Pat. Off. . |
| 95 01803 | 1/1995 | WIPO . |
| 96/14070 | 5/1996 | WIPO . |
| 97 02017 | 1/1997 | WIPO . |

Primary Examiner—James M. Spear
Attorney, Agent, or Firm—Ellen Ciambrone Coletti

[57] ABSTRACT

The present invention concerns pharmaceutical dosage forms comprising cisapride-(L)-tartrate or a precursor form thereof, contained in a porous structure consisting essentially of one or more polymers which are insoluble or practically insoluble in water or gastro-intestinal fluids and wherein the pores of the porous structure comprise a substance soluble in water or gastro-intestinal fluids adjacent to the surface of the dosage form. The present invention is further concerned with processes for preparing such pharmaceutical dosage forms and with the use of these pharmaceutical dosage forms as a medicine, especially in treating gastro-intestinal disorders, more particularly gastro-oesophagal reflux disease.

6 Claims, No Drawings

CISAPRIDE SUSTAINED RELEASE

CROSS-REFERENCE TO RELATED APPLICATIONS

This application is based upon PCT Application Ser. No. PCT/EP 96/05346, filed Nov. 26, 1996, which claims priority from European Patent Application Ser. No. 95.203.309.0, filed on Dec. 1, 1995.

The present invention concerns pharmaceutical dosage forms comprising cisapride-(L)-tartrate or a precursor form thereof, contained in a porous structure consisting essentially of one or more polymers which are insoluble or practically insoluble in water or gastrointestinal fluids and wherein the pores of the porous structure comprise a substance soluble in water or gastrointestinal fluids adjacent to the surface of the dosage form. The present invention is further concerned with processes for preparing such pharmaceutical dosage forms and with the use of these pharmaceutical dosage forms as a medicine, especially in treating gastrointestinal disorders, more particularly gastro-oesophagal reflux disease.

European Patent No. 0,076,530 discloses the gastroprokinetic agent cisapride and classic compositions thereof. Cisapride has the following structural formula:

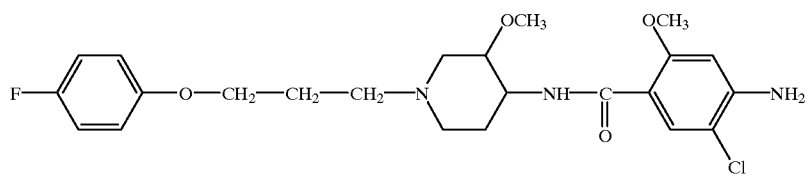

The systematic chemical name of cisapride is cis-4-amino-5-chloro-N-[1-[3-(4-fluorophenoxy)propyl]-3-methoxy-4-piperidinyl]-2-methoxybenzamide. Cisapride is a racemic mixture of two enantiomers. Cisapride has excellent gastrointestinal motility stimulating properties and is reported to be devoid of antidopaminergic activity. Its utility in a variety of gastro-intestinal disorders has already been reported extensively. It is currently being marketed as a medicine to treat the symptoms of gastro-oesophagal reflux disease, dyspepsia and other conditions which are related to impaired gastrointestinal motility.

The present dosage forms of cisapride call for an intake of cisapride tablets at least twice a day. A more patient-friendly intake regimen and consequently a intake regimen which would enhance patient compliance, would be a once-daily dosing frequency. A dosage form allowing once-daily intake of cisapride is provided with the sustained-release formulation of the present invention.

The terms "sustained-release", "extended-release" and "slow-release" are to be considered as synonyms in the context of the present invention.

Useful extended-release formulations of cisapride for oral administration should release the active ingredient, i.e. cisapride, over a long period of from 12 to 30 hours, preferably from 15 to 24 hours, that is throughout the whole gastrointestinal tract with its varying pH values. However, the solubility of cisapride depends very much on the surrounding pH. The solubility of cisapride is the highest in a strongly acidic medium at pH 1 to 2, such as for example in gastric juice. The solubility diminishes rapidly when the pH of the (physiological) medium increases, for example in the intestines. An effective sustained-release formulation of cisapride should therefore function not only in highly acidic but also in less acidic or neutral media. Moreover an extended-release formulation should release the active ingredient as soon as the formulation is administered and should release the active ingredient in a constant manner, preferably following zero order to first order kinetics. This profile is desired because it provides relief to the patient very soon after administration and overdosing is avoided upon consecutive administration the formulation.

A solution to the problem of very pH-dependent solubility of cisapride was found in the use of (+)-cis-4-amino-5-chloro-N-[1-[3-(4-fluorophenoxy)propyl]-3-methoxy-4-piperidinyl]-2-methoxybenzamide [R(R*,R*)]-2,3-dihydroxybutanedioate (1:1)-referred to hereinunder as "cisapride-(L)-tartrate". Cisapride-(L)-tartrate is the salt of racemic cisapride with (+)-L-tartaric acid and is exemplified in European Patent No. 0,076,530 as compound number 241.

In comparison with other salts of cisapride the salt form with [R(R*,R*)]-2,3-dihydroxybutanedioic acid, i.e. (+)-L-tartaric acid (the natural form of tartaric acid) shows a remarkably good solubility in water. Cisapride being a racemic mixture and L-tartaric acid being one single enantiomer, the resulting salt form is in principle a mixture of two diastereomeric salts: (+)-cisapride-(L)-tartrate and (−)-cisapride-(L)-tartrate.

Unexpectedly, it was shown that the salt cisapride-(L)-tartrate is a mixture of the diastereomers [(3R4S)(2R3R)] and [(3S4R)(2R3R)], that crystallize as a double salt in a 1:1 ratio. (This is confirmed by X-ray.) The (3R4S) and (3S4R) refer to the respective enantiomers of cisapride and the (2R3R) refers to the optically pure L-tartrate.

It was found that formulations containing cisapride-(L)-tartrate released cisapride in a racemic form, i.e. equal amounts of (+)-cisapride and (−)-cisapride or in other words the diastereomeric salt forms (+)-cisapride-(L)-tartrate and (−)-cisapride-(L)-tartrate unexpectedly have equal dissolution rates.

Moreover, it was also found that during the preparation of cisapride-(L)-tartrate no enrichment of one of the two diastereomeric salt forms could be detected.

Our copending application PCT/EP95/04198 discloses a matrix-formulation wherein cisapride-(L)-tartrate is embedded in a mixture of viscous polymers. Said copending application also discloses the preparation of cisapride-(L)-tartrate.

The problem with this kind of matrix formulations is that when such matrix formulation is ingested concomitantly with food, the formulation may rapidly erode due to (amongst others) mechanical stress and give rise to an undesired immediate release of the active ingredient.

This problem is solved by using the dosage forms as described hereinunder which are more resistant to the mechanical strains that are exerted on the dosage form when ingested concomitantly with food. Hence, the object of the present invention is to provide a slow-release preparation, in which the dissolution rate of the active substance is substantially constant over a long period of time. This means that the rate determining characteristics of the coating is substantially independent of any mechanical influence, enzymes, surface tension, pH and salt concentration or ionic strength.

The present invention encompasses a pharmaceutical dosage form comprising cisapride-(L)-tartrate or a precursor form thereof, contained in a porous structure consisting essentially of one or more polymers which are insoluble or practically insoluble in water or gastrointestinal fluids and wherein the pores of the porous structure comprise adjacent to the surface of the dosage form a substance soluble in water or gastro-intestinal fluids.

Pharmaceutical dosage forms which are particularly envisaged are sustained-release tablets, particularly suitable for oral administration.

Cisapride-(L)-tartrate is released from this dosage form. Cisapride-(L)-tartrate can be present as such or can be formed in situ. In the latter case a precursor of cisapride-(L)-tartrate is present.

Polymers insoluble in water or gastrointestinal fluids are for instance synthetic resins, polyamide, cellulose acetate, ethyl cellulose or practically insoluble polyvinyl alcohol. Other examples are uncrosslinked copolymers of hydrophobic monomers components and hydrophylic monomer components, wherein the hydrophobic component is selected from at least one ester of an unsaturated acid of the general formula $CH_2=CRCOOR^1$, where R is hydrogen or $CH_3$ and $R^1$ is a linear or branched chain alkyl group and wherein the hydrophilic monomer component is selected from one or more N-vinyl pyrrolidone, acrylic or methacrylic acid of the general formula $CH_2=CRCOOR^2$, where R is hydrogen or methyl and $R^2$ is a hydroxy terminated alkyl or alkyloxy group.

Said polymers may be cross-linked or non-cross-linked. Said polymers may be swellable or non-swellable.

Mixtures of such polymers are also envisaged. Said insoluble or practically insoluble polymers should be pharmaceutically acceptable.

A first embodiment of the present invention provides for a firmly coherent skeleton structure consisting of a insoluble or practically insoluble polymer, such as, a pharmaceutically acceptable synthetic resin. The structure includes pore-like interconnected canals or ducts open to the exterior of the structure and a material which contains cisapride-(L)-tartrate, which is soluble in the fluid contained in such canals or ducts. In this type of pharmaceutical dosage form the active ingredient, i.e. cisapride-(L)-tartrate, may be present in the pores as a solid.

When exposed to the gastro-intestinal fluids the material containing cisapride-(L)-tartrate slowly dissolves thus releasing the active ingredient. Adjacent to the surface of the dosage form said pores may be filled with a substance soluble in water or gastro-intestinal fluids other than cisapride-(L)-tartrate itself.

A second embodiment of the present invention provides for a slow-release tablet consisting of a drug containing core comprising cisapride-(L)-tartrate and a coating on said core. The coating consists of a polymer substance which remains substantially intact and insoluble in water or gastrointestinal fluids. Fine particles of a readily water-soluble substance are randomly distributed in the coating. When in contact with water or gastrointestinal fluids these substances, readily dissolve in said fluids and thus the pores are "opened" or "formed". Therefore, said readily water-soluble substances are also called "pore-forming substances". The said polymer coating may be a polyamide, cellulose acetate, ethyl cellulose or low water soluble polyvinyl alcohol. Examples of such coatings are found in GB 1,186,990 and U.S. Pat. No. 3,538,314.

The pore-forming substance used according to the present invention should be water-soluble and pharmaceutically acceptable. An interesting pore-forming substance is saccharose (sucrose). Other substances which may be used include polyvinyl pyrrolidone, sodium chloride, and polyethylene glycol of higher molecular weight such as 1500 g/mol, 4000 g/mol or 6000 g/mol.

The pore-forming substance is preferably but not necessary insoluble in the solvent used for coating the tablets. The particle size of the pore-forming substance may preferably vary between 0.5 and 50 $\mu$m.

In a special embodiment of the present invention the pore-forming substance is cisapride (L)-tartrate itself.

In another special embodiment of the present invention the insoluble polymers comprises a readily soluble acid, preferably tartaric acid or a acidic buffer-forming substance. This embodiment has the additional advantage that a acidic micro-environment can be created near the surface of the dosage form. This acidic micro-environment may obviate potential clogging of some or all pores when some of the cisapride-(L)-tartrate is converted into a less soluble salt such as, for example, cisapride hydrochloride formed during transit through the stomach. Although formation of a less soluble salt is not a problem in the stomach because of the acidity of the environment in the stomach, it can form a problem once the dosage form enters the intestinal system which is much less acidic. If the less soluble salt of cisapride is still present in the pores, the less acidic environment of the intestines may cause the less soluble salt of cisapride to precipitate, thus clogging the pores of the dosage form.

The presence of acid or acidic buffer-forming substance in the pores can obviate this problem.

The problem of potential clogging may be solved be other ways, for instance, by applying another coating comprising a readily soluble acid or an acidic buffer.

The term acidic buffer as used hereinabove refers to buffer systems that create an acidic environment wherein cisapride is soluble.

In yet another special embodiment of the present invention the pore-forming substance is a mixture of the above-mentioned pore-forming substances.

As explained above, when the coating is exposed to gastrointestinal fluids, the pore-creating substance is dissolved and pores are generated. During manufacture, the pore-forming particles are randomly distributed over the tablet surface and in the polymer layer. The dissolution medium, i.e. water or gastrointestinal fluids, then penetrates through the pores into the core or tablet proper and dissolves the drug contained therein. The solution which forms inside the membrane then diffuses out through the pores. The diffusion rate depends on a number of factors such as the number of pores, pore size, the solubility of the drug in the gastrointestinal fluid. These parameters can readily be controlled and they can also be varied within broad limits. The diffusion rate through the membrane is governed by the concentration gradient between the inside and the outside of the membrane and, as long as any drug in solid form is present inside the membrane, the interior drug concentration will be fairly constant. The drug concentration outside the membrane is very small due to the large volume of dissolution medium and the fact that the drug is continuously absorbed by the gastrointestinal system of the patient.

A particularly interesting coating is described in EP 0,211,991, published Mar. 4, 1987 and consists essentially of a terpolymer of polyvinyl chloride, polyvinyl acetate and polyvinyl alcohol and a pore-forming substance being randomly distributed in the terpolymer.

The pore-forming substance may preferably be present in an amount of 1–20 parts for each 1–10 parts of polymer.

The method of producing the coated tablet according to the invention comprises the steps of dissolving the polymer or the mixture of polymers in a suitable solvent, preparing a suspension or solution of the pore-forming substance, providing a pharmaceutical tablet, combining the suspension or solution of pore-forming substance and solvent solution of the polymer or the mixture of polymers to form a coating fluid, applying the coating fluid in the form of a solution or suspension to the tablet, and drying the coating fluid on the tablet to provide a polymer-coated tablet having the water-soluble pore-forming substance randomly distributed within the coating.

The starting preparations are produced in the following manner:

1) A polymer or a mixture of polymers is dissolved in a suitable solvent or mixture of solvents.

2) The pore-forming particles are ground either by dry milling in a ball mill or by wet-milling in a glass bead milling device to a defined particle size, preferably between 0.5 and 50 $\mu$m. The particles are dispersed in the above mentioned suitable solvents or mixtures or solvents and mixed with the polymer solution.

3) The thus formed coating fluid, in the form of a solution or suspension, is then applied on drug containing cores by a conventional coating procedure. Examples of such coating procedures are pan coating, manual or spray coating, Wurster coating, and other fluid-bed containing procedures.

Plasticizers may also be used in the coating fluid to improve the elasticity of the membrane during packaging and transport. Plasticizers are generally used in concentrations between 0.2 and 4 % (w/w) in the coating fluid, depending both on the coating fluid composition and the elasticity demands of the final product. Representative examples of suitable plasticizers are acetyltributylcitrate, polyethyleneglycols.

Coloring matter can also be incorporated in the coating fluid.

The amount of coating is dependent upon factors such as, for example, the intended release time as well as the solubility of the cisapride-(L)-tatrate in the core composition. The amount of coating ranges from 5 mg to 200 mg of coating (w/w).

The drug containing core mentioned hereabove may comprise, apart from cisapride-(L)-tartrate, art-known excipients such as lactose, maize starch, microcristalline cellulose, polyvidone, magnesium stearate, colloidal anhydrous silica and polysorbate.

A second coating can be applied, and may contain one or more same or different drugs, for which rapid release is desirable. Preferably said second coating comprises cisapride, cisapride-(L)-tartrate or a precursor thereof. This coating fluid is preferably a water-based sugar coating and therefore, a seal coating between the latter and the terpolymer membrane coating is frequently necessary or desirable.

The present dosage form preferably comprises from about 1 to 100 mg of active ingredient, interestingly the amount of active ingredient ranges from 20 mg to 40 mg.

The pharmaceutical dosage form, subject of the present invention, is to be used a medicine for treating gastrointestinal disorders, such as, gastroparesis, either idiopathic or associated with diabetic neuropathy, anorexia nervosa, after vagotomy or partial gastrectomy (the symptoms mainly consist of early satiety, anorexia, nausea and vomiting); symptoms of X-ray or endoscopy negative upper digestive discomfort, characterized by early satiety, postprandial fullness, inability to finish a normal sized meal, bloating, excessive belching, anorexia, nausea, vomiting or by ulcer-like complaints (epigastric burning or pain), gastro-oesophageal reflux disorders, including the curative and maintenance treatment of oesophagitis; in babies: chronic and excessive regurgitation or vomiting, when positional and dietary measures have failed; intestinal pseudo-obstruction, associated with motility dysfunctions resulting in insufficient propulsive peristalsis and in stasis of gastric and intestinal contents; restoration of colonic propulsive motility as a long-term treatment of chronic constipation. Consequently, the present invention further provides for a method of treating gastrointestinal disorders, especially gastro-oesophagal reflux disease.

What is claimed is:

1. A pharmaceutical dosage form in the form of a sustained-release coated tablet comprising cisapride-(L) tartrate or a precursor form thereof, contained in a coating comprised of a porous structure consisting essentially of a terpolymer of polyvinyl chloride, polyvinyl acetate and polyvinyl alcohol and wherein the pores of the coating comprise adjacent to the surface of the dosage form a substance soluble in water or gastro-intestinal fluids.

2. A coated tablet as claimed in claim 1, wherein the substance soluble in water or gastro-intestinal fluids is saccharose, sodium chloride, polyvinylpyrrolidone or polyethylene glycol.

3. A coated tablet as claimed in claim 1 wherein the substance soluble in water or gastro-intestinal fluids is cisapride-(L)-tartrate or a precursor thereof.

4. A coated tablet as claimed in claim 1 wherein the coated tablet is coated with a second outer coating.

5. A coated tablet as claimed in claim 4 wherein said second outer coating comprises cisapride, cisapride-(L)-tartrate or a precursor thereof.

6. A process of preparing a tablet as claimed in claim 1 comprising the steps of dissolving the polymer or the mixture of polymers in a suitable solvent, preparing a suspension or solution of the substance, providing a pharmaceutical tablet, combining the suspension or solution of pore-forming substance and solvent solution of the polymer or the mixture of polymers to form a coating fluid, applying the coating fluid in the form of a solution or suspension to the tablet, and drying the coating fluid on the tablet to provide a polymer-coated tablet having the water-soluble pore-forming substance randomly distributed within the coating.

* * * * *